United States Patent
Radke et al.

(10) Patent No.: US 6,786,075 B2
(45) Date of Patent: Sep. 7, 2004

(54) METHOD FOR THE MEASUREMENT OF AEROSOL PARTICLES IN GASEOUS SAMPLES

(75) Inventors: Friedrich Radke, Graz (AT); Peter W. Krempl, Graz (AT); Christian Reiter, Graz (AT)

(73) Assignee: AVL List GmbH, Graz (AT)

(*) Notice: Subject to any disclaimer, the term of this patent is extended or adjusted under 35 U.S.C. 154(b) by 0 days.

(21) Appl. No.: 10/124,677

(22) Filed: Apr. 17, 2002

(65) Prior Publication Data

US 2002/0178784 A1 Dec. 5, 2002

(30) Foreign Application Priority Data

Apr. 18, 2001 (AT) ............................................. 626/2001

(51) Int. Cl.⁷ ............................................. G01N 29/02
(52) U.S. Cl. .................... 73/24.06; 73/24.06; 73/23.31; 73/28.01
(58) Field of Search ............................. 73/24.06, 23.31, 73/28.01

(56) References Cited

U.S. PATENT DOCUMENTS

| | | | | |
|---|---|---|---|---|
| 3,561,253 A | * | 2/1971 | Dorman | 73/24.03 |
| 4,446,720 A | * | 5/1984 | Sinclair | 73/24.06 |
| 4,518,861 A | * | 5/1985 | Krempl et al. | 250/339.09 |
| 4,827,760 A | * | 5/1989 | Saito | 73/28.01 |
| 5,349,844 A | * | 9/1994 | Lilienfeld | 73/28.01 |
| 5,892,141 A | * | 4/1999 | Jones et al. | 73/24.03 |

FOREIGN PATENT DOCUMENTS

| | | | | |
|---|---|---|---|---|
| GB | 0779510 A2 | * | 3/1994 | G01N/1/22 |
| GB | 0586118 A2 | * | 6/1997 | G01N/27/00 |

* cited by examiner

*Primary Examiner*—Hezron Williams
*Assistant Examiner*—André K. Jackson
(74) *Attorney, Agent, or Firm*—Sonnenschein Nath & Rosenthal LLP

(57) ABSTRACT

A process to determine aerosol particles in gaseous samples, specifically in the exhaust of diesel motors, includes the at least indirect deposit of aerosol particles on a piezoelectric oscillating crystal and the determination of the oscillation parameters of the piezoelectrically stimulated oscillation of the crystal. In order to assure the required reproducibility reliably and independently of the type of aerosol particles, and thus to achieve a high quality of measurements, the piezoelectric crystal is charged to oscillation during less than half the period of deposit of aerosol particles.

18 Claims, 3 Drawing Sheets

Fig. 5

Aerosol

Apparatus to Vacuum pump

METHOD FOR THE MEASUREMENT OF AEROSOL PARTICLES IN GASEOUS SAMPLES

BACKGROUND OF THE INVENTION

The invention concerns a process to determine aerosol particles in gaseous samples, specifically in the exhaust of diesel motors, including the at least indirect deposit of aerosol particles on a piezoelectric oscillating crystal and the determination of the oscillation parameters of the piezoelectrically stimulated oscillation of the crystal element.

Emissions of diesel motors are classified primarily by the particle concentration and the particle number, where the measurement of the particle concentration places increasingly more stringent demands upon the technology of measurement. It is presently not possible to carry out a measurement at low emission levels and/or a measurement with high temporal resolution.

The particle concentration is normally measured by the deposition of particles in filters or by deposits on substrata. Deposits on substrata involve impact or electrostatic deposits in most measurement processes. The amount of particles deposited is then measured as the difference of the weight of the filters or substrata before and after the exposure, from which the concentration can then be calculated.

These measurement processes yield the accumulated particle weight within a measurement cycle. The disadvantages of both methods are the high degree of imprecision of the weight measurement, especially at low particle weights, and the lack of temporal resolution within a measurement cycle.

Use of the crystal micro scale is a process that does not exhibit the disadvantages specified above; it provides a signal with high temporal resolution and is especially well suited for the determination of small weights. This process uses the weight sensitivity of a piezoelectric crystal, which is equipped with electrodes and which may be charged into mechanical oscillations, onto which the particles are deposited. The deposited particle layer causes the resonance frequency of the crystal element to decrease, where the amount of decrease provides a measurement of the deposited particle weight.

This process is described in U.S. Pat. No. 3,561,253 and in a novel arrangement in EP 0 779 510 A2. According to U.S. Pat. No. 3,561,253, the deposition of particles on the quartz crystal, which is equipped with electrodes, involves impact or electrostatic deposits. The measurement of the change in resonance frequency of the system, consisting of the quartz crystal and the oscillator, is based on a frequency counter. EP 0 779 510 A2 describes an apparatus consisting essentially of a deposit component, an oscillating element with means to determine the frequency and a heating element; this apparatus allows for a subsequent thermal gravimetric analysis. As EP 0 779 510 A2 points out, such apparatus produces changes in the resonance frequency of merely a few hundred Hertz with injection of diesel particles.

The capabilities of such a system are shown in the determination of layer thickness in thin film technology. Such sensors yield modifications of the resonance frequency of up to 1 MHz, the layer thickness can be determined to just a few nm, and the behavior of the sensor due to the deposited layer can be described theoretically with great precision, assuming that the deposited layers have the properties of solids and that they can be produced in a reproducible manner.

However, this is normally not the case for diesel particles, because normally the formation involves flocculation and accumulation in a layer structure that is not very dense. It can be shown that the oscillation of the crystal will not compress the deposited particle layer, as would have been expected.

SUMMARY OF THE INVENTION

It is an object of the present invention to present an improved process to measure aerosol particles, which guarantees the required reproducibility and thus a high quality of measurements that is reliable and independent of the type of aerosol particles.

This objective is achieved by stimulating the piezoelectric crystal to oscillation during less than half the period of deposits of the aerosol particles. This process significantly improves the deposit of particles on the crystal during rest periods of the crystal and leads to the formation of a homogeneous particle layer on the surface, which enlarges the measurement range and significantly improves the reproducibility of the measurement.

According to an additional characteristic of the invention, it is possible to design the system such that a portion of the sample is fed into a second apparatus that takes continuous measurements, where at least one of these measurement values is calibrated gravimetrically by use of at least one measurement value that was determined from the oscillation parameters of the piezoelectrically stimulated oscillation of the crystal.

Many types of continuous processes have the disadvantage that it is generally not possible to derive a gravimetric signal from the measurement values, because a change of the system to be measured causes such changes in the measurement values that it is not possible to derive a specification of a generally valid calibration factor relating the measurement value and the gravimetric signal to be derived from it. However, for short time intervals and for known weights of aerosol particles, it is possible to derive a calibration factor applicable to that time interval. It is advantageous then to determine a calibration factor for the continuous measurement process during specific time intervals from the weight deposited on the piezoelectric crystal.

A particularly advantageous embodiment provides for the continuous measurement by the at least indirect deposit of aerosol particles on a second piezoelectric oscillating crystal and the determination of the oscillation parameters of the piezoelectrically stimulated oscillation of the second crystal element.

However, the objective stated above is also achieved by an additional characteristic of the invention, namely that at least a portion of the sample is fed to a second apparatus that takes continuous measurements, where at least one of these measurement values is calibrated gravimetrically by at least one of the measurement values determined from the oscillation parameter of the piezoelectrically stimulated oscillation of the crystal element. This calibration guarantees the reproducibility of the measurements of the continuous process independent of potential modifications of the measurement value not caused by the system to be measured.

A further characteristic of the invention enables a variation that is particularly efficient at saving time, where the sample is divided and is fed to both measurement processes simultaneously. This variation is also suited for the combination of measurement processes, which do not modify the sample, with processes, which modify the sample in definable parameters, such as by deposits on a piezoelectric crystal or by deposit in a filter.

If only small volumes or amounts of the sample are available, an alternative embodiment of the present invention will often be more useful, where the sample is fed sequentially to both measurement processes. However, it is significant here that the first process in the sequence does not modify the sample or modifies it only in those properties that are not to be measured by the subsequent process.

A first embodiment of the invention as a continuous measurement process relies on the determination of the quantity of light dispersed by the aerosol particles.

An alternative embodiment of the invention in turn uses a process where the continuous measurement process relies on the determination of the quantity of light absorbed by the aerosol particles in the gaseous sample.

It is advantageous for both of the just specified embodiments of the invention that the sample is first fed to the continuous measurement process and subsequently to the process with at least indirect deposit of aerosol particles on a piezoelectric oscillating crystal, because the continuous measurement processes in question will not modify the properties to be measured by the piezoelectric process.

BRIEF DESCRIPTION OF THE DRAWING

The following description is intended to describe the invention by reference to the included drawings of preferred embodiments.

FIG. 5 is the depiction of an apparatus for the simultaneous operation of a continuous optical measurement process and a process for deposition on a piezoelectrically charged crystal, where preferably one of these processes excites the piezoelectrically charged crystal for significantly less than half the deposition period for aerosol particles on the other crystal.

DETAILED DESCRIPTION OF THE PREFERRED EMBODIMENT

Figure 1:
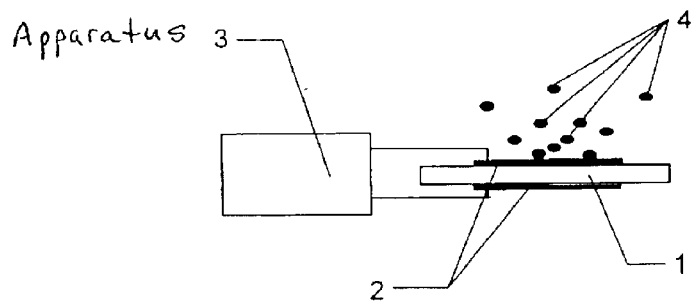
FIG. 1 shows a schematic depiction of the measurement apparatus with a piezoelectrically charged crystal, upon which the aerosol particles are deposited.

The sensor of the measurement apparatus shown in FIG. 1 comprises of a piezoelectric crystal 1 with electrodes 2, and apparatus 3 for the piezoelectric stimulation of the crystal for mechanical oscillations and sensitive surfaces, which are generally identical to electrodes 2, where the aerosol particles 4 are at least indirectly deposited. A deposit usually involves impact, low-pressure impact or electrostatic deposit. It is advantageous that apparatus 3 can also specify the duration of piezoelectric stimulation, the scanning duration, and the temporal frequency of piezoelectric stimulation, the scanning interval.

The invention also assumes that piezoelectric crystal 1 is charged to oscillations for less than one-half of the deposition period of aerosol particles. It is advantageous that scanning is scheduled for the end of the deposition period for each scanning interval. The deposition period of aerosol particles on crystal 1 may be subdivided into several scanning intervals, during which crystal 1 is charged once by apparatus 3. It is advantageous that the scanning intervals are of equal length over the entire deposition period of particles on crystal 1 and, though not necessarily linked, also that the scanning duration is of equal length in each scanning interval.

The linkage of this measurement process with a continuous measurement process makes it possible that the signal of crystal 1 can be used for the gravimetric calibration of the continuous process. Depending on whether or not the aerosol is modified by the continuous process, the apparatus may be either in parallel (the aerosol is divided into two components and is fed to both measurement systems) or in series (the aerosol is fed through the continuous measurement apparatus and is then deposited in total or in part at the crystal). It is an advantage of the serial arrangement that the same sample is used for the gravimetric measurement.

Figure 2:
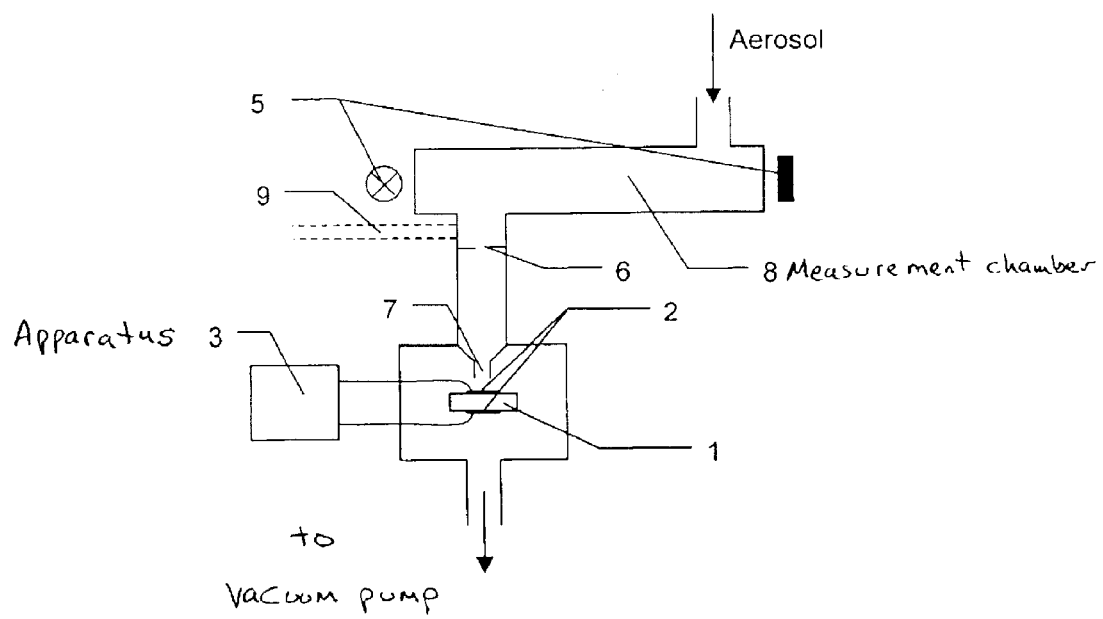
FIG. 2 is a depiction of a continuous optical measurement process with a subsequent process for deposition on a piezoelectrically charged crystal.

As FIG. 2 shows, it is possible to use a continuous measurement process, such as an opacimeter 5, 8 in series with crystal 1. The measurement parameter of the continuous process is the loss in intensity of a light ray due to the aerosol particles present in measurement chamber 8, measured with a light source and a sensor 5. The particle deposit on electrodes 2, i.e., the sensitive surfaces of crystal 1 then involves low-pressure impact. If the entire aerosol stream is not to be fed to the electrodes, which is necessary particularly in the case of high particle concentrations, because measurement is feasible only at low weight input unless sampling is restricted to short time periods, release tube 9 can be used to divert a portion of the aerosol prior to deposit on crystal 1. The low-pressure impact sensor consists of the critical nozzle 6 to generate the low pressure and to stabilize the flow simultaneously and an impact nozzle 7 for the defined deposit of aerosol particles on crystal 1.

Figure 3:
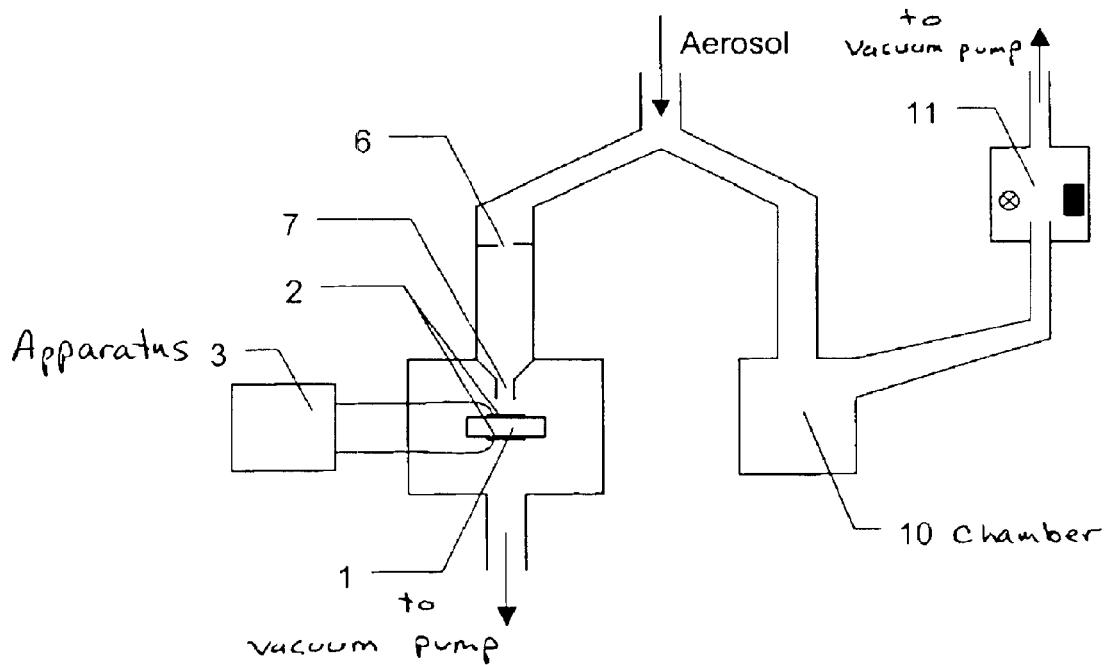
FIG. 3 shows an apparatus for the simultaneous operation of a continuous optical measurement process and a process for deposition on a piezoelectrically charged crystal.

FIG. 3 depicts an apparatus with a condensation particle counter (CPC). The measurement processes are arranged in parallel. The particle flow in the CPC is first fed into a chamber 10, which is satiated with alcohol vapor, where the particles enlarge and are counted by an optical system in measurement chamber 11. The deposition of particles on crystal 1 uses a low-pressure impact nozzle arrangement 6, 7, as described for FIG. 2. In lieu of a CPC, this apparatus could also use an electrical aerosol analyzer (EAA). The classification according to size in the EAA uses differences in electrical mobility of the particles that were electrically charged by a corona discharge prior to entry into the measurement chamber. The number of particles in each size category is computed from the electrical charge sensed by the collection electrode.

Figure 4:
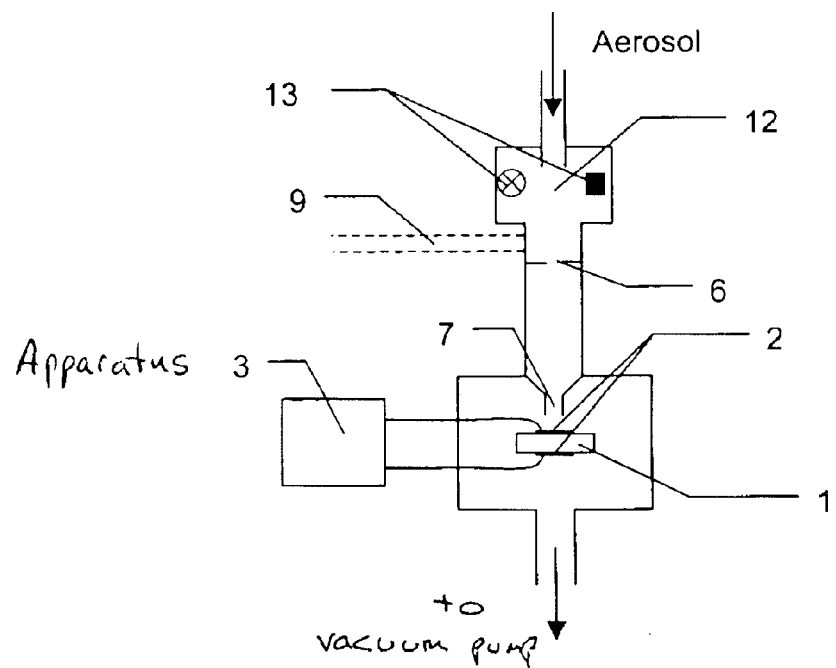
FIG. 4 shows an additional embodiment of a continuous optical measurement process with a subsequent process for deposition on a piezoelectrically charged crystal.

A continuous measurement process can also rely on the scattering of light by the particles, which is shown in the example in FIG. 4. Because this light scattering process does not modify the aerosol particles, this apparatus may be included in series with a process involving deposits on a piezoelectrically charged crystal 1. The aerosol is fed into measurement chamber 12 that includes a system 13 for the measurement of light scattering. The subsequent particle deposits then once again involve a low-pressure impact nozzle arrangement 6, 7. The release tube 9 can be used to divert a portion of the aerosol flowing towards crystal 1.

Figure 5:
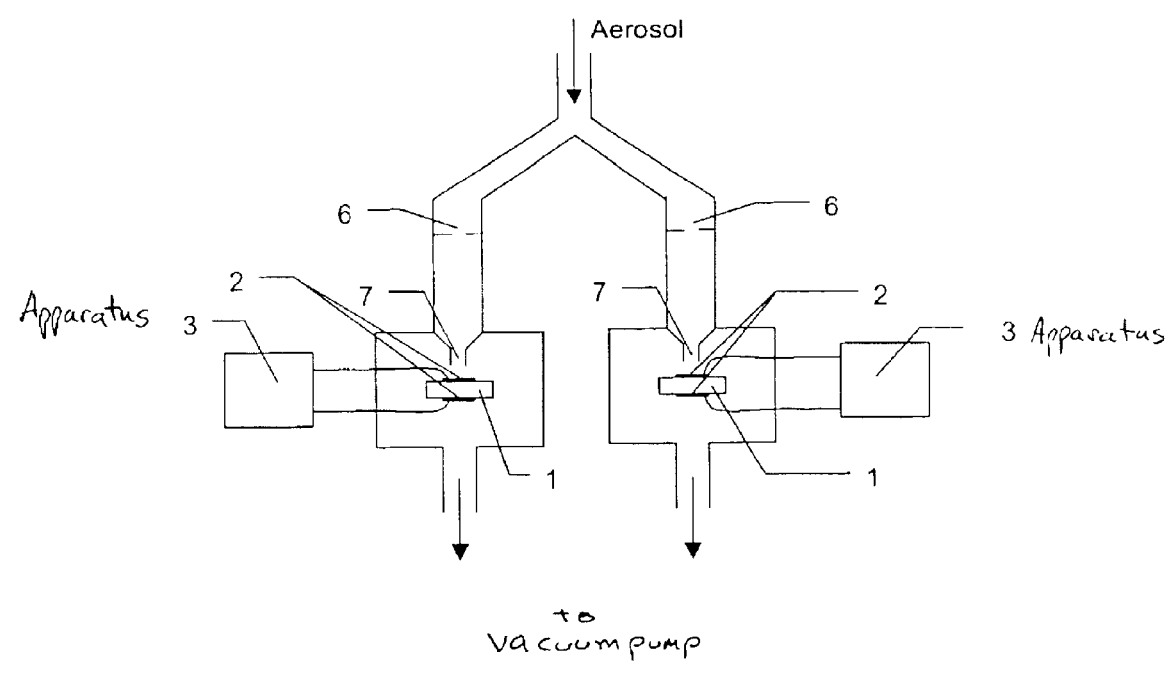

Systems, in which the weight is to be determined with a high temporal resolution, may be designed to include a piezoelectric crystal in the continuous measurement process as well. FIG. 5 shows the measurement design with two crystals 1 in parallel. In the continuous system, piezoelectric crystal 1 is charged throughout the entire duration of the measurement, whereas the calibration system delivers a charge only in specified scanning intervals with a specified duration of scanning, as is described in more detail above in connection with FIG. 1.

The gravimetric calibration of the continuous measurement process takes place in successive defined time intervals. During these intervals, the accumulated particle weight on crystal 1 is determined, thus retroactively calibrating the signal for the continuous measurement apparatus.

As is apparent from the foregoing specification, the invention is susceptible of being embodied with various alterations and modifications which may differ particularly from those that have been described in the preceding specification and description. It should be understood that we wish to embody within the scope of the patent warranted hereon all such modifications as reasonably and properly come within the scope of our contribution to the art.

What is claimed is:

1. A method for the measurement of aerosol particles in gaseous samples, comprising the steps:
   at least indirectly depositing aerosol particles on a piezoelectric oscillating crystal for a deposition period;
   exciting crystal oscillations for a scanning duration;
   determining oscillation parameters of a piezoelectrically stimulated oscillation of the crystal during said scanning duration,
   said excitation of the crystal oscillation being done during the deposition period; and said scanning duration being less than half the deposition period.

2. A method according to claim 1, including the step of leading at least a portion of the sample into a second apparatus that determines continuous measurement values, where at least one of the measurement values is gravimetrically calibrated by a measurement value that was determined by the oscillation parameter of the piezoelectrically charged oscillations of the crystal.

3. A method according to claim 2, wherein the continuous measurement also includes at least indirect deposits of aerosol particles on a second piezoelectric oscillating crystal and a determination of the oscillation parameter of the piezoelectrically charged oscillations of the second crystal.

4. A method according to claim 2, wherein the sample is divided and fed to the two measurement processes in parallel.

5. A method according to claim 2, wherein the sample is fed to the two measurement processes sequentially.

6. A method according to claim 2, wherein the continuous measurement process utilizes a scattering of light by the aerosol particles.

7. A method according to claim 6, wherein the sample is led first to the continuous measurement process and then to a process that relies on the at least indirect deposit of aerosol particles on a piezoelectric oscillating crystal.

8. A method according to claim 2, wherein the continuous measurement process utilizes an extinction of light due to the aerosol particles contained in the gaseous sample.

9. A method according to claim 8, wherein the sample is led first to the continuous measurement process and then to a process that relies on the at least indirect deposit of aerosol particles on a piezoelectric oscillating crystal.

10. A method according to claim 1, wherein said gaseous sample comprises an exhaust from a diesel motor.

11. A method for the measurement of aerosol particles in gaseous samples, comprising the steps:
    at least indirectly depositing aerosol particles on a piezoelectric oscillating crystal,
    exciting crystal oscillations for a scanning duration:
    determining oscillation parameters of a piezoelectrically stimulated oscillation of the crystal during said scanning duration to achieve a measurement value,
    leading at least a portion of the sample into a second apparatus that continuously takes measurement values, where at least one of the measurement values is gravimetrically calibrated by at least one of the measurement values that were determined by the oscillation parameter of the piezoelectrically excited oscillations of the crystal.

12. A method according to claim 11, wherein the sample is divided and fed to the two measurement processes in parallel.

13. A method according to claim 11, wherein the sample is fed to the two measurement processes sequentially.

14. A method according to claim 11, wherein the continuous measurement process utilizes a scattering of light by the aerosol particles.

15. A method according to claim 14, wherein the sample is led first to the continuous measurement process and then to a process that relies on the at least indirect deposit of aerosol particles on a piezoelectric oscillating crystal.

16. A method according to claim 11, wherein the continuous measurement process utilizes an extinction of light due to the aerosol particles contained in the gaseous sample.

17. A method according to claim 16, wherein the sample is led first to the continuous measurement process and then to a process that relies on the at least indirect deposit of aerosol particles on a piezoelectric oscillating crystal.

18. A method according to claim 11, wherein said gaseous sample comprises an exhaust from a diesel motor.

* * * * *